United States Patent [19]

Choulet et al.

[11] 4,212,991
[45] Jul. 15, 1980

[54] SINGLE-STAGE PROCESS FOR THE PREPARATION OF TEREPHTHALIC ACID

[75] Inventors: Jean-Claude Choulet, Meyzieu; Andre Laily, Venissieux, both of France

[73] Assignee: Rhone-Poulenc Industries, Paris, France

[21] Appl. No.: 794,134

[22] Filed: May 5, 1977

[30] Foreign Application Priority Data

May 11, 1976 [FR] France .................................. 76 14867

[51] Int. Cl.$^2$ ............................................. C07C 51/02
[52] U.S. Cl. .................................. 562/480; 562/481; 562/485; 562/486
[58] Field of Search .................... 260/515 P; 562/480, 562/481, 485, 486

[56] References Cited

U.S. PATENT DOCUMENTS 2,846,468  8/1958  York .................................. 260/515 P

FOREIGN PATENT DOCUMENTS 41-14575  8/1966  Japan ...................................... 562/486
975113  11/1964  United Kingdom ...................... 562/482

Primary Examiner—Jane S. Myers
Attorney, Agent, or Firm—Burns, Doane, Swecker & Mathis

[57] ABSTRACT

Highly pure terephthalic acid is prepared from di-potassium terephthalate. The terephthalic acid so produced aids in the direct production of high quality polyester fiber.

9 Claims, No Drawings

SINGLE-STAGE PROCESS FOR THE PREPARATION OF TEREPHTHALIC ACID

BACKGROUND OF THE INVENTION

1. Field of the Invention

The present invention relates to a process for the preparation of terephthalic acid from its di-potassium salt. The process produces high purity terephthalic acid which can be used in the direct preparation of high quality polyester fibers.

2. Description of the Prior Art

It is well known to the art that di-potassium terephthalate is a common starting material in the industrial production of terephthalic acid. In such production schemes, the di-potassium terephthlate is generally obtained by the dismutation of potassium benzoate at elevated temperatures. This process, commonly known as the Henkel process in the chemical art, has been the subject of numerous patents. It is described, for example, in French Patent No. 2,143,401.

The conversion of di-potassium terephthalate derived via the dismutation of potassium benzoate has also been the subject of extensive research and development. The most valuable of these processes involve the reaction of di-potassium terephthalate with benzoic acid. Their advantage lies in their ability to produce, in addition to terephthalic acid, potassium benzoate which can be directly recycled in the production sequence to obtain additional di-potassium terephthalate by dismutation.

It too has been proposed to convert di-potassium terephthalate to terephthalic acid using benzoic acid in processes comprising one or more reaction stages. It is generally recognized that the conversion of di-potassium terephthalate to terephthalic acid can be best accomplished in two stages. During the first stage di-potassium terephthalate is reacted with benzoic acid to yield solid potassium hydrogen terephthalate. During the second stage the potassium hydrogen terephthalate is converted to terephthalic acid using an additional quantity of benzoic acid. Such processes are described, for example, in French Patent Nos. 1,170,781, 1,335,202 and 2,140,168, in British Patent No. 975,113 and in U.S. Pat. No. 2,846,468.

Some processes for the preparation of terephthalic acid from di-potassium terephthalate have been proposed in which all of the benzoic acid is fed into a single reaction zone. Such processes are described in Japanese Patent No. 14,575/66 and U.S. Pat. No. 2,846,468. According to these processes, a nearly saturated aqueous solution of di-potassium terephthalate is reacted with excess benzoic acid. When the reaction is complete, the solid phase, consisting of terephthalic acid, benzoic acid and potassium benzoate, is separated and recovered. Thereafter, the solid mixture is suspended in water and heated. This purification treatment must be repeated several times to obtain terephthalic acid of satisfactory acid number. However, it has been demonstrated that the terephthalic acid prepared by these processes is not suitable for the direct preparation of high quality polyester fibers.

Thus, there remains a need in the art for a method of preparing terephthalic acid in a single reaction zone which results in the production of highly pure terephthalic acid which can be used in the direct preparation of high quality polyester fiber.

SUMMARY OF THE INVENTION

Accordingly, it is a primary object of the present invention to provide an improved process for the production of highly pure terephthalic acid.

Another object of the invention is to provide an improved process for the preparation of terephthalic acid by reacting di-potassium terephthalate and benzoic acid in a single stage operation.

Yet another object of the invention is to provide a method for preparing highly pure terephthalic acid which can be used in the direct preparation of high quality polyester (polyalkylene terephalate, preferably polyethylene terephthalate) fibers.

Other objects, features and advantages of the invention will become more apparent from the description which follows.

It has now been determined that the foregoing objects of the invention are readily attained by a new, improved process for the preparation of terephthalic acid by reacting di-potassium terephthalate and benzoic acid in an aqueous medium containing potassium benzoate. More particularly, the process comprises a single stage operation composed of the following sequential steps: [a] di-potassium terephthalate and benzoic acid are contacted in an aqueous medium containing potassium benzoate, at a temperature greater than about 80° C., the quantities of the constituents being selected such that there is initially less than about 0.40 mole of di-potassium terephthalate per kg of water, between about 0.05 and 1.2 moles of potassium benzoate per kg of water, and the molar ratio of benzoic acid to di-potassium terephthalate is between about 4 and 12, [b] terephthalic acid is separated from the reaction mixture by conventional means, such as by filtration or centrifugation, at temperatures greater than about 80° and [c] the recovered terephthalic acid is subjected to a purification treatment.

DETAILED DESCRIPTION OF THE INVENTION

According to a preferred embodiment of the invention, the conversion of di-potassium terephthalate is conducted in a dilute medium containing potassium benzoate. The presence of potassium benzoate within the appropriate concentration range results in the preparation of pure terephthalic acid by preventing the precipitation of benzoic acid, which benzoic acid is present in free or complexed form.

Although the subject invention is particularly useful in converting di-potassium terephthalate obtained by the dismutation of potassium benzoate (commonly known in the chemical art as the Henkel process), it must be understood that its utility is not so limited. Rather, the invention applies to the conversion of any di-potassium terephthalate to terephthalic acid, irrespective of the origin of the di-potassium salt. Moreover, the mixture introduced into the reaction zone can contain various types of impurities depending upon the process utilized for the preparation of the di-potassium terephthalate. For example, when the Henkel process is employed, the feed into the reaction zone may contain minor amounts of di-potassium o-phthalate, di-potassium iso-phthalate, and the potassium salts of benzenetricarboxylic acids existing as position isomers.

The temperature is usually maintained between about 80° and 250° C. and preferably between about 90° and 150° C. in the reaction zone, which comprises at least one agitated reactor. Generally, from about 0.1 to 0.40 mole of di-potassium terephthalate per kg of feed water is charged into the reaction zone. The quantity of potassium benzoate initially introduced is preferably between about 0.2 and 0.8 mole per kg of water. A portion of the potassium benzoate may come from the dismutation zone if the degree of dismutation of the potassium benzoate is not quantitative. The necessary initial addition of potassium benzoate can be made with fresh potassium benzoate, but it is often more convenient to recycle a portion of the mother liquor obtained after separation and recovery of the terephthalic acid. The molar ratio of benzoic acid to di-potassium terephthalate in the feed is preferably between about 5 and 8.

The speed of agitation of the reactor or reactors in the reaction zone may vary. Generally, agitation speeds are selected which evidence the greatest degree of efficiency in the particular process being employed.

The constituents in the feed can be introduced into the reaction zone by any appropriate means. For example, the feed may be divided into three streams, one comprising the aqueous solution of di-potassium terephthalate obtained from the dismutation of potassium benzoate, another comprising benzoic acid and the third comprising water and the necessary quantity of potassium benzoate.

According to another embodiment of the invention, the reaction zone is divided into several reaction subzones, i.e., a series of reactors, or a single reactor with separate compartments. In such cases it may be desirable to divide the supply of feed streams into fractions which are introduced directly into the various subzones. However, the required quantity of potassium benzoate must always be fed into the first reaction subzone.

Crystalline terephthalic acid is separated and recovered at the outlet of the reaction zone by any conventional method, such as filtration or centrifugation. The separation process is conducted at temperatures greater than about 80° C. and preferably between about 85° and 160° C. Thereafter, a final purification of the terephthalic acid is performed by any known method. For example, the purification may utilize organic solvents such as alcohols, ketones and aromatic hydrocarbons (methanol, ethanol, acetone, benzene, toluene and the like) but it is preferred to use an aqueous treatment. Thus, the terephthalic acid crystals may be purified by simply washing in hot water (the water usually being maintained at temperatures between about 80° 250° C. and preferably between about 90° and 150° C.). It is also possible to re-suspend the terephthalic acid crystals in hot water, which may require the use of several stages, or to dissolve and re-precipitate the crystals in water by sequential heating and cooling. In all cases, the liquor which has been used in the aqueous purification treatment can be recycled into the reaction zone. In this manner, potassium benzoate is recycled to the reaction zone.

The process of the invention can be performed discontinuously. However, a continuous process is preferred.

In order to further illustrate the present invention and the advantages thereof, the following specific examples are given, it being understood that their purpose is solely illustrative and in no way limitative.

EXAMPLE 1

1.67 kg/hr of di-potassium terephthalate, 5.49 kg/hr of benzoic acid, 1.00 kg/hr of potassium benzoate and 22.4 kg/hr of water were fed continuously into an agitated reactor maintained at 160° C.

After the reaction, the mixture from the reactor was conveyed into a suction filter which operated isothermally at 100° C. Terephthalic acid containing 20% water was separated therein at the rate of 1.18 kg/hr. The terephthalic acid crystals were then washed by introducing hot water at the rate of 2 kg/hr into the suction filter.

The washing liquor was recycled into the reactor. 0.98 kg/hr of pure terephthalic acid was finally obtained after drying.

EXAMPLE 2

1.62 kg/hr of di-potassium terephthalate, 8.24 kg/hr of benzoic acid, 0.74 kg/hr of potassium benzoate and 21.45 kg/hr of water were fed continuously into an agitated reactor maintained at 200° C.

This feed was obtained by introducing the aqueous solution of di-potassium terephthalate obtained from the dismutation reaction, benzoic acid, the washing liquor used in the aqueous purification treatment of the terephthalic acid crystals, and 3% of the mother liquor obtained after separation of the terephthalic acid crystals.

After the reaction, the mixture was conveyed into a suction filter which operated isothermally at 150° C. The mother liquor and 1,055 g/hr of terephthalic acid, containing 18.5% water, were separated therein. The terephthalic acid crystals were then re-suspended in 2,000 g of hot water (150° C.). Thereafter 1,050 g/hr of wet terephthalic acid were separated in a suction filter. After drying, 0.87 kg/hr of terephthalic acid was obtained, with the following characteristics:

Acid number: 675
Benzoic acid content: 90 ppm
Content of other benzene-carboxylic acids: <10 ppm
Potassium content: <1 ppm
Ash content: <5 ppm
Average particle size: 95μ
(90% of the material had a particle size greater than 25μ)

This acid was useful in the direct preparation of high quality polyester fiber.

EXAMPLE 3

The reaction zone consisted of three agitated reactors maintained respectively at 220° C., 180° C. and 150° C. The aqueous solution of di-potassium terephthalate obtained from the dismutation reaction, the liquor from washing the terephthalic acid crystals and 37% by weight of the mother liquor obtained after separation of the terephthalic acid were fed into the first reactor. The benzoic acid was fed into each reactor, at the rate of 4.67 kg/hr into the first reactor and at the rate of 1.98 kg/hr into the other two reactors. The overall feed into the first reactor was as follows:

Di-potassium terephthalate: 2.17 kg/hr
Benzoic acid: 4.67 kg/hr
Potassium benzoate: 2.54 kg/hr
Water: 69.5 kg/hr After the reaction, the reaction mixture leaving the third reactor was conveyed into a suction filter. The mother liquor was separated at 150° C., a portion of the liquor being recycled into the first reactor, and 1.35 kg/hr of wet terephthalic acid, containing about 16% water, was isolated.

Thereafter the terephthalic acid crystals were washed by introducing hot water at the rate of 2.5 kg/hr into the suction filter. The washing liquor was recycled into the first reactor. After drying, 1.13 kg/hr of pure terephthalic acid was finally obtained.

While there have been described and pointed out the fundamental novel features of the invention as applied to the preferred embodiment, those skilled in the art will appreciate that various modifications, changes, and omissions in the process for the preparation of terephthalic acid described and illustrated can be made without departing from the spirity of the invention. It is the intention, therefore, to be limited only by the scope of the claims which follow.

What is claimed is:

1. A process for the preparation of highly pure terephthalic acid comprising reacting di-potassium terephthalate with benzoic acid in an aqueous reaction medium containing potassium benzoate, wherein the initial composition of reactants introduced into said reaction zone comprises less that about 0.40 mole of di-potassium terephthalate per kg of water, between about 0.2 and 0.8 moles of potassium benzoate per kg of water and between about 4 to 12 moles of benzoic acid per mole of di-potassium terephthalate and wherein the reaction zone is maintained at temperatures greater than about 80° C.

2. The process as defined by claim 1, wherein the reaction is conducted in a reaction zone comprising at least one agitated reactor.

3. The process as defined by claim 2, wherein terephthalic acid is separated from the reaction mixture at the outlet of said reaction zone as a solid.

4. The process as defined by claim 3, wherein the separation of terephthalic acid from the reaction mixture is conducted at temperatures greater than about 80° C.

5. The process as defined by claim 3, wherein the terephthalic acid separated from the reaction mixture is subjected to a purification treatment.

6. The process as defined by claim 5, wherein the purification treatment is an aqueous treatment.

7. The process as defined by claim 3, wherein the residual reaction mixture is recycled into the reaction zone and provides the required amount of potassium benzoate.

8. The process as defined by claim 2, wherein about 0.1 to 0.4 mole of di-potassium terephthalate per kg of water, about 0.2 to 0.8 mole of potassium benzoate per kg of water and about 5 to 8 moles of benzoic acid per mole of di-potassium terephthalate are initially introduced into the reaction zone, said zone being maintained at a temperature between about 80° and 250° C.

9. The process as defined by claim 1, wherein the reactant di-potassium terephthalate is produced by dismutation of potassium benzoate.

* * * * *